United States Patent
Dornburg et al.

(10) Patent No.: US 6,200,750 B1
(45) Date of Patent: Mar. 13, 2001

(54) MAMMALIAN HOMOLOGOUS RECOMBINATION ACTIVATING SEQUENCES AND METHOD OF IDENTIFICATION AND THEIR USE THEREOF

(75) Inventors: Ralph Dornburg, Lansdale; Paul K. Olson, Maple Glen, both of PA (US)

(73) Assignees: Thomas Jefferson University; University of Medicine and Dentistry, both of NJ (US)

( * ) Notice: Subject to any disclaimer, the term of this patent is extended or adjusted under 35 U.S.C. 154(b) by 0 days.

(21) Appl. No.: 08/935,532

(22) Filed: Sep. 23, 1997

Related U.S. Application Data

(60) Provisional application No. 60/025,762, filed on Sep. 23, 1996.

(51) Int. Cl.[7] .............................. C12Q 1/68; C12N 15/64
(52) U.S. Cl. ............................................... 435/6; 435/91.4
(58) Field of Search ...................... 435/6, 91.4; 536/23.1

(56) References Cited

U.S. PATENT DOCUMENTS 5,814,479 * 9/1998 Zhou et al. ........................ 435/69.1

OTHER PUBLICATIONS

Shiroishi, et al, "Hotspots of Homologous Recombination in Mouse Meiosis" *Adv. Biophys.*, vol. 31, pp. 119–132, (1995).

William P. Lafuse, Ph.D., "Molecular Biology of Murine MHC Class II Genes" *Critical Reviews in Immunology*, vol. 11(3,4,), pp. 167–194, (1991).

Hutchinson, et al., "Hotspots of Homologous Recombination" *Experientia*, vol. 50, pp. 234–241, (1994).

Olson, et al., "Unusually High Frequency of Reconstitution of Long Terminal Repeats in U3–Minus Retrovirus Vectors by DNA Recombination or Gene Conversion" *Journal of Virology*, vol. 66, No. 3, pp. 1336–1343, (1992).

Olson, et al., "Improved Self–Inativating Retroviral Vectors Derived from Spleen Necrosis Virus" *Journal of Virology*, vol. 68, No. 11, pp. 7060–7066, (1994).

Ralph Dornburg, "Reticuloendotheliosis Viruses and Derived Vectors" *Gene Therapy*, vol. 2, pp. 301–310, (1995).

Dixon, et al., "Mutagenesis of Cauliflower Mosaic Virus" *Gene*, vol. 25, pp. 189–199, (1983).

Shinnick, et al., "Nucleotide Sequence of Moloney Murine Leukaemia Virus" *Nature*, vol. 293, No. 15, pp. 543–548, (1981).

Dornburg, et al., "Presence of a Retroviral Encapsidation Sequence in Nonretroviral RNA Increases the Efficiency of Formation of cDNA Genes" *Journal of Virology*, vol. 64, No. 2, pp. 886–889, (1990).

Dornburg, et al., "cDNA Genes Formed after Infection with Retroviral Vector Particles Lack the Hallmarks of Natural Processed Pseudogenes" *Molecular and Cellular Biology*, vol. 10, No. 1, pp. 68–74, (1990).

Dornburg, et al., "Retroviral Vector System for the Study of cDNA Gene Formation" *Molecular and Cellular Biology*, vol. 8, No. 6, pp. 2328–2334, (1988).

Watanabe, et al., "Construction of a Helper Cell Line for Avian Reticuloendotheliosis Virus Cloning Vectors" *Molecular and Celular Biology*, vol. 3, No. 12, pp. 2241–2249, (1983).

Kawai, et al., "New Procedure for DNA Transfection with Polycation and Dimethyl Sulfoxide" *Molecular and Cellular Biology*, vol. 4, No. 6, pp. 1172–1174, (1984).

Myers, et al. "X and The RecBC D Enzyme of *Escherichia coli*" *Annu. Rev. Genet.*, vol. 28, pp. 49–70, (1994).

Hu, et al., "Genetic Consquences of Packaging Two RNA Genomes in One Retroviral Particle: Pseudodiploidy and High Rate of Genetic Recombination" *Proc. Natl. Assoc. Sci.*, USA, vol. 87, pp. 1556–1560, (1990).

Hu, et al., "Retroviral Recombination and Reverse Transcription" *Science*, vol. 250, pp. 1226–1233, (1990).

* cited by examiner

Primary Examiner—W. Gary Jones
Assistant Examiner—Jehanne Sovaya
(74) Attorney, Agent, or Firm—Dechert Price & Rhoads (57) ABSTRACT

Methods of identifying homologous recombination activators are provided. These recombination activators can be use for gene therapy.

16 Claims, 5 Drawing Sheets

```
prD17   ATGCGGCATCAGAGCAGATTGTACTGAGAGTGCACCATACTA
pRA2    ............................---C.........
pRA4    ..........................................
pRA9    ..........................................

Band 1
prD17   GAGGATC----CCCGGGCGACTCAGTCAATCGGAGGACTGGC
prA2    .......CCCACCC............................
pRA4    .......CCCACCC............................
pRA9    .......CCCACCC............................

prD17   CCCCGAGTGAGGGGTTGTGGGCTTTTTATTGAG-CTGGGGA
pRA2    ................................C......G
pRA4    ................................-.......
pRA9    .............---------------------------- prD17   GCAGAAGCGCGC-GAACAGAAGCGAGAAGCAACTGATTGG   [SEQ ID NO:1]
pRA2    ............-..........................   [SEQ ID NO:2]
pRA4    ............-..........................   [SEQ ID NO:3]
pRA9    ----------..G..........................   [SEQ ID NO:4]
```

MAMMALIAN HOMOLOGOUS RECOMBINATION ACTIVATING SEQUENCES AND METHOD OF IDENTIFICATION AND THEIR USE THEREOF

RELATED APPLICATIONS

This application claims benefit of U.S. Provisional Patent Application No. 60/025,762 filed Sep. 23, 1996.

The present invention is directed to homologous recombination events and methods of identifying DNA sequences which direct the same. Methods of gene therapy are also provided in which genetic recombination is directed using DNA sequences identified in accordance with the present invention.

Recognition of cis-acting DNA signals occupies a central role in both site-specific and general recombination pathways, wherein genetic material or the sequence thereof can be exchanged from one polynucleotide to another, resulting in recombinant, i.e., new, sequences of the polynucleotide receiving the genetic material or the sequence thereof Signals in site-specific pathways define the points at which the exchange will occur. General signals do not promote defined rearrangements but rather create "hotspots" by increasing the frequency of homologous recombination in their vicinity. A well-studied general signal is the crossover hotspot instigator (chi) found in *Escherichia coli* (*E. Coli*), which functions at the inception of the recombination. Although hotspots exist in eucaryotes, specific signals, mostly nuclease sites, have only been demonstrated in yeast. The recombination hotspots observed in higher eucaryotes typically lie near regions of highly repetitive sequence and are generally observed in the context of meiosis. Shiroishi et al., *Adv. Biophy.*, 31:119–132 (1995); Lafuse, *Crit. Rev. Immunol*, 11:167–194 (1991); Smith, *Experientia*, 50:234–241 (1994). Although the existence of ubiquitous, general somatic recombination signals have been proposed, nothing comparable to chi has been functionally identified Smith, *Experientia*, 50:234–241 (1994).

SUMMERY OF THE INVENTION

In accordance with the present invention is provided a system for identifiing DNA sequences that promote homologous recombination in mammalian cells comprising a library of self-inactivating retroviral vectors containing random DNA sequence inserts.

Methods of identifying DNA sequences that promote homologous recombination in mammalian cells are also provided. Such methods comprise providing a library of self inactivating retroviral vectors containing random DNA inserts and performing at least two rounds of replication by transfecting mammalian packaging cells with the retroviral vector library. Replicated vectors are recovered and sequenced wherein sequences of DNA inserts contained in recovered vectors promote homologous recombination in mammalian cells.

Therapeutic methods are also provided in accordance with the present invention wherein a patient suffering from a DNA viral infection is administered an effective amount of a construct comprising a recombination activator linked to an inactivated viral gene.

DEFINITIONS

The following terms shall have, for the purposes of this application, the respective meanings set forth below. In particular, for the purpose of interpreting the claims, the term definitions shall control over any assertion of a contrary meaning based on other text found herein:

"cis-acting" means the influence of a polynucleotide sequence on the recombination activity of another polynucleotide sequence that is located on the same chromosome.

"construct" or "constructs" means a polynucleotide that includes a recombination activator.

"homologous recombination" means genetic exchange between polynucleotides that have identical or nearly identical base sequences.

"metazoan" means a multicellular animal.

"motif" means a sequence that promotes or activates homologous recombination.

"pharmaceutical composition" means a combination comprising a construct and a pharmaceutically-acceptable carrier or diluent.

"random DNA sequence inserts" means unselected sequences of DNA with respect to recombination promoting activity that are inserted into a SIN vector using conventional methods of molecular biology.

"recombination-competent cell" means a cell having the requisite enzymes for recombination between homologous polynucleotides.

"round of replication" operationally means the transfection of a retroviral vector comprising DNA into a cell that is known to be a host for the retrovirus from which the retroviral vector is derived, whereupon the transfected vector is replicated by synthesizing the retroviral RNA genome using cellular RNA polymerases, and completing the round by synthesizing the complementary DNA thereto using viral reverse transcriptase.

"self-inactivating vector" or "SIN vector" is a retroviral vector having the retroviral genome sequence except for a deletion in the U3 region of the right LTR that precludes self-replication of the retrovirus upon the insertion of the vector into a cell.

DETAILED DESCRIPTION

Figure 1A:
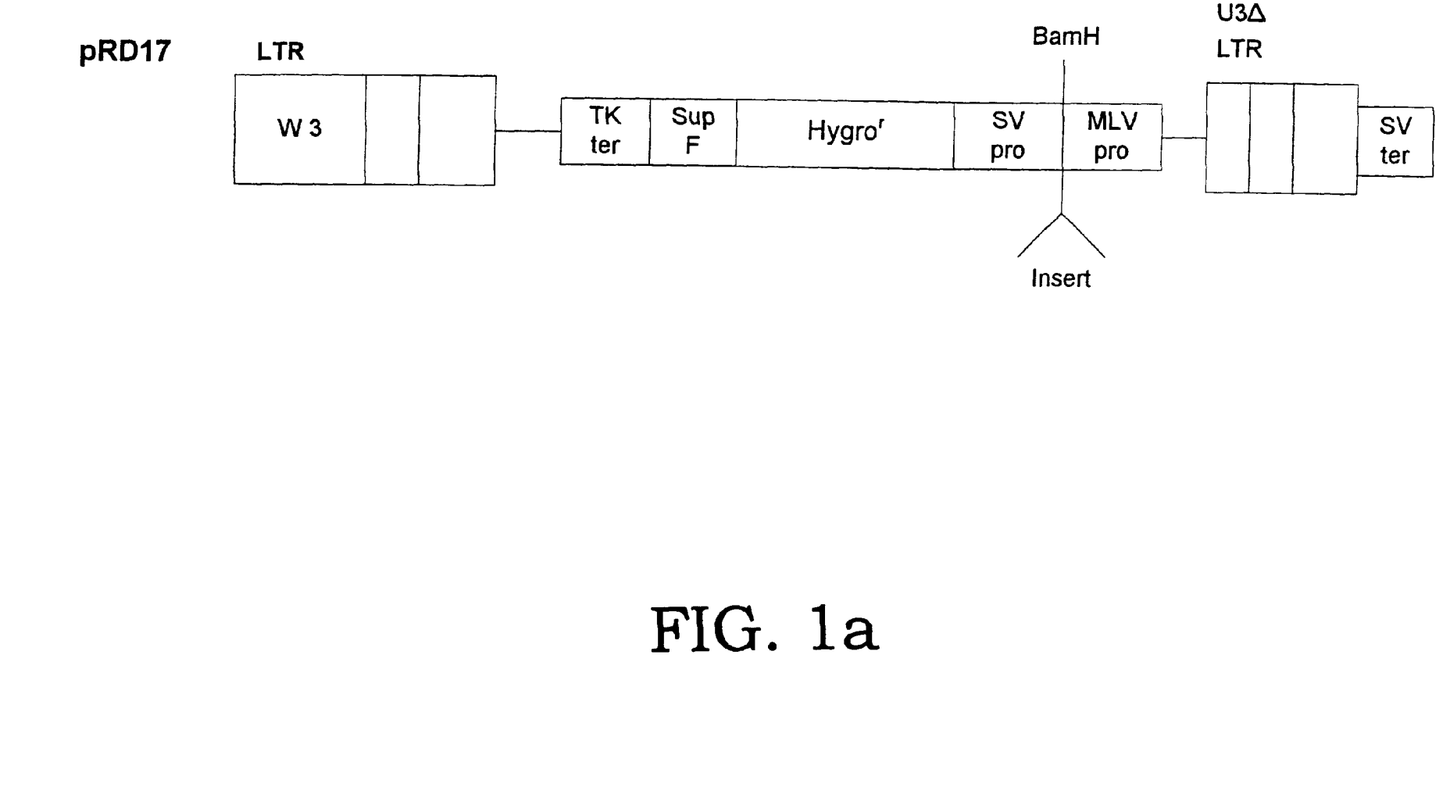
FIG. 1A is a schematic representation of the self-inactivating retroviral vector, pRD17.
Figure 1B:
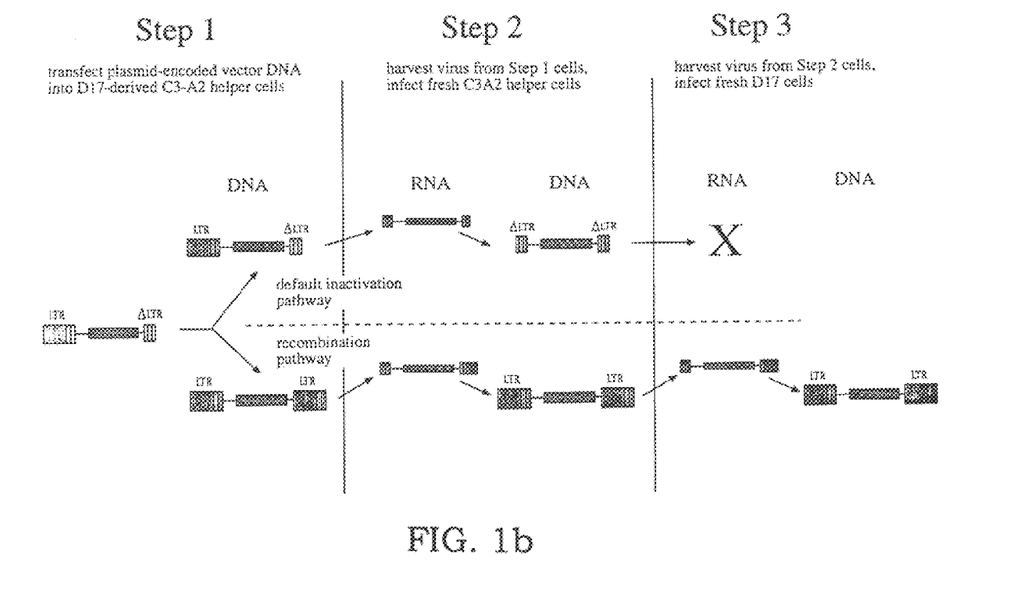
FIG. 1B is a schematic representation of the methods of capturing mammalian recombination activating sequences by performing two or more replicating steps.

The present invention provides methods of identifying DNA sequences which promote homologous recombination, referred to herein as recombination activators (RA). For this purpose, one or more self-inactivating (SIN) retroviral vectors including random DNA inserts are provided. Such SIN retroviral vectors include preferably retroviral left and right long terminal repeats (LTRs), as are known in the art Preferably, such SIN retroviral vectors include a replication-blocking mutation in the right LTR; more preferably such SIN retroviral vectors include deletions of the U3 region of the right LTR region. Preferred such SIN retroviral vectors include vectors of the pRD line, including pRD17, pRDl8, pRD33, and pRD48, all of which contain the aforementioned deletions. One particularly preferred vector, pRD17, is shown in FIG. 1. Random DNA is inserted into the vector backbone, as known in the art.

The homologous recombination promoted by the aforementioned RAs can occur in any recombination-competent cell, including, but not limited to, that of a metazoan. Preferably the metazoan cells are mammalian; more preferably, human.

Random DNA can be prepared by any number of methods known to those skilled in the art. For instance, random DNA oligonucleotides may be prepared by solid state synthesis using standard phosphoramidite chemistry. Alternatively, chromosomal DNA can be digested to provide random DNA inserts.

As shown in FIG. 1, libraries of SIN retroviral vectors with random DNA inserts can be used to identify sequences that promote homologous recombination by transfecting packaging cells with the library. Packaging cells, as used herein, refer to cells which are sensitive to the chosen self-inactivating retrovirs. In particular, packaging cells of the present invention must contain replication machinery for the retrovirus. In accordance with the present invention, the packaging cells are preferably mammalian cells. In particular, C3A2 packaging cells are preferred in some embodiments of the invention, although any suitable cell will suffice, the suitability of which pertains to the possession of replication machinery for the retrovirus by the cell. In a preferred embodiment, once an RA is identified, the requirement for the retrovirus sensitive packaging cells ceases as the RA can be used to promote recombination in any recombination competent cell, as noted above.

Vectors of the library that contain a sequence that promotes homologous recombination will "escape" inactivation by a recombination event, and thus will be able to complete more than one round of replication. In accordance with the present invention, more than one round of replication is performed. Preferably, at least two rounds of replication are carried out. Each round of replication is performed by transfecting fresh packaging cells with the retroviral vector library. At any time after the second round of replication, the retroviral vectors which contain recombination activators may be identified, recovered and sequenced, using conventional means. Identification can be, for instance, by use of a marker gene, such as a marker gene that confers antibiotic resistance. The sequences of the recovered retroviral vector preferably promote homologous recombination in, for example, metazoan cells; more preferably in mammalian cells; and yet more preferably, in human cells.

Such sequences can be used therapeutically. By linking the recombination activator with a DNA sequence substantially homologous to a gene or DNA sequence of interest, recombination can be promoted at a selected site, thereby replacing genomic DNA with a selected exogenous, "insertional" DNA sequence. This "insertional DNA construct" may be used to block, correct, or ameliorate a genetic disease or condition or to inactivate an active, but undesirable gene within a host cell. Thus, depending upon the end result sought, the insertional DNA construct can encode a defective copy of an undesirable gene or a fully functional copy of a desired gene of which an ineffective copy is included in the genome of an individual by virtue of heredity, mutation, or infection, or a combination thereof For instance, a construct can be prepared whereby the recombination activator is linked to a viral gene critical to the replication or packaging of a DNA virus infecting a patient. DNA viruses such as Epstein Barr virus, human immunodeficiency virus, papilloma viruses, and cytomegalovirus can be treated using methods of the invention. The construct is prepared by linking a gene encoding an essential structural protein or protein essential for replication of the virus with a recombination activator. The gene is preferably substantially homologous to the gene of interest but has incorporated within the sequence one or more inactivating mutations that prevent transcription or result in an inactive protein following transcription. Other gene therapy treatments can include, but is not limited to, insertion of functional genes encoding enzymes or structural proteins that are defective in such genetic diseases as cystic fibrosis, Tay-Sachs disease, muscular dystrophy, and the like.

The recombination activator sequence is preferably less than 30 base pairs in length and should be linked closely to the insertional gene of interest, such as, for example, within about 1,000 nucleotides, more preferably, about 500 nucleotides, yet more preferably, within about 50 nucleotides. Gene sequences of interest are well known in the art and can be determined from published sequences or by sequencing a gene of interest. For purposes of the present invention, substantially homologous means at least about 75% identical in sequence. Greater than 90% identity in sequence is still more preferred. The construct can be prepared by methods known to those skilled in the art.

Vectors may be constructed using any cloning plasmid. The resulting plasmid will contain a copy of a target gene and a recombination activator sequence in close proximity thereto. In preferred embodiments the recombination activator sequence is no more than about 1000 bp upstream or downstream from the defective gene. Alternatively, the recombination activator sequence can be located withini an intron of the gene. In still other embodiments of the present invention the recombination activator sequence is located within an exon of the gene. The cloning vector may be any cloning vector or other DNA known to those skilled in the art for use in assembling cloned genes.

Preferably, the recombination activator is selected from one of the following groups: CCCA, CCCACC, CCCACCC, and compounds of the formula wherein $R_1$ and $R_2$ are respectively any nucleotide or nucleotides, n and m are the same or different and are integers between 0 and 1000, wherein at least one of n and m is non-zero, and Z is the DNA sequence identified by the present method as promoting homologous recombination. Z is preferably CCCA, CCCACC, or CCCACCC; more preferably CCCACC or CCCACCC; most preferably CCCACCC. Any stretch of nucleic acid residue denoted by either R group, where n is greater than 1, may be either a heteropolymer or a homopolymer. Preferably, the R groups are each less than about five nucleotides; more preferably, less than about 10 nucleotides; yet more preferably, less than about 25 nucleotides; and most preferably, less than about 50 nucleotides. Preferably, n and m are each between 1 and 4; and more preferably, can each be up to about 10.

The construct is administered to a patient suffering from a viral infection. Recombination events at the site of the critical viral gene will result in inactivation of the viral gene of interest, thereby ameliorating or eliminating the viral infection Alternatively, a construct is administered to a patient suffering from a genetic disease associated with a gene mutation. Recombination events at the site of the critical gene will result in replacement of the mutant gene with a functional gene of interest, thereby ameliorating or eliminating the genetic condition. The terms "gene mutation" or "genetic disease" as used herein is any gene which is not expressed in the normal population and is associated with a deleterious physical condition. Cystic fibrosis is one example of a genetic disease which can be addressed using methods of the present invention.

Constructs can be formulated for therapeutic applications of mammals by those having ordinary skill in the art. The dosage range of a construct to be administered to mammals, particularly humans, to be effective in the treatment of viral infections and genetic conditions and disorders can be determined by those having ordinary skill in the art.

Pharmaceutical preparations incorporating one or more constructs of the present invention are used in the method that is the invention, and are referred to herein as pharmaceutical compositions. The method that is the invention relates to treatment of viral infections and genetic conditions and disorders by administration of effective amounts of a pharmaceutical compositions that comprise constructs disclosed herein. The constructs used in the method that is the invention can be formulated for human or other mammalian therapeutic applications by those having ordinary skill in the arL The plasmid may be delivered to target cells using a variety of delivery methods such as liposomes or viral vectors including, but not limited to adenoviral vectors, herpes virus-derived vectors and SV40-derived vectors. Alternatively the plasmid may be delivered directly with or without conjugation to protein or protein complexes.

The mode of administration of constructs and pharmaceutical compositions that includes such constructs includes any means that produces contact of the active ingredient with the agent's site of action in the body of a mammal or in a body fluid or tissue. These modes of administration include, but are not limited to, oral, topical, hypodermal, intravenous, intramuscular and intraparenteral methods of administration. In practicing the method that is the invention, the constructs may be administered singly or two or more such constructs, can be administered in concert, or the construct or constructs can be administered in combination with pharmaceutically active compounds, such as chemotherapeutic compounds, or in conjunction with other therapies, such as radiation treatment. In the method that is the invention, the construct or constructs are preferably administered in combination with a pharmaceutically-acceptable carrier selected on the basis of the selected route of administration and standard pharmaceutical practice; such combinations are referred to herein as pharmaceutical compositions, as noted above.

The method may include administration of the construct or constructs to mammals, preferably humans, in therapeutically effective amounts. The dosage administered in any particular instance will depend upon factors such as the pharmacodynamic characteristics of the compound of the invention, its mode and route of administration; age, health, and weight of the recipient; nature and extent of symptoms; kind of concurrent treatment, frequency of treatment, and the effect desired.

It is contemplated that the daily dosage of a construct used in the method that is the invention will be in the range of from about 1 μg to about 100 mg per kg of body weight, preferably from about 100 μg to about 40 mg per kg body weight, more preferably from about 1 mg to about 20 mg per kg per day, and most preferably 1 mg to about 10 mg per kg per day. Pharmaceutical compositions can be administered in a single dosage, divided dosages or in sustained release. Persons of ordinary skill are able to determine dosage forms and amounts with only routine experimentation based upon the considerations of this invention.

The method of administering constructs and pharmaceutical compositions include administration of same as a pharmaceutical composition orally in solid dosage forms, such as capsules, tablets, and powders, or in liquid dosage forms, such as elixirs, syrups, and suspensions. The constructs and pharmaceutical compositions can also be administered parenterally in sterile liquid dosage forms or topically in a carrier. The construct or constructs can be formulated into dosage forms according to standard practices in the field of pharmaceutical preparations. See *Remington's Pharmaceutical Sciences*, A. Osol, Mack Publishing Company, Easton, Pa.

Constructs can be mixed with powdered carriers, such as lactose, sucrose, mannitol, starch, cellulose derivatives, magnesium stearate, and stearic acid for insertion into gelatin capsules, or for forming into tablets. Both tablets and capsules can be manufactured as sustained release products for continuous release of medication over a period of hours. Compressed tablets can be sugar or film coated to mask any unpleasant taste and protect the tablet from the atmosphere or enteric coated for selective disintegration in the gastrointestinal tract.

Liquid dosage forms for oral administration can contain coloring and flavoring to increase patient acceptance, in addition to a pharmaceutically acceptable diluent such as water, buffer or saline solution.

For parenteral administration, a construct or constructs can be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound. Stabilizing agents, antioxidizing agents and preservatives can also be added. Suitable antioxidizing agents include sodium bisulfite, sodium sulfite, and ascorbic acid, citric acid and its salts, and sodium EDTA Suitable preservatives include benzalkonium chloride, methyl- or propyl-paraben, and chlorbutanol.

The present invention in another embodiment also relates to the substantially purified polynucleotide identified in accordance with the aforementioned method for identifyingg DNA sequences that promote homologous recombination. By "substantially purified," it is intended that the identified DNA sequences are at least about 90% free of other DNA sequences, more preferably at least about 95% free, yet more preferably at least about 99% free. Non-polynucleotide components can be included with the substantially purified polynucleotides, such as, but not limited to, proteins, carbonmydrates, and salts.

The invention also includes polynucleotides of the formula:

$$(R_1)_n\text{---}Z\text{---}(R_2)_m,$$

wherein $R_1$ and $R_2$ are respectively any nucleotide or nucleotides, n and m are the same or different and are integers between 0 and 1000, wherein at least one of n and m is non-zero, and Z is the DNA sequence identified by the present method as promoting homologous recombination. Z is preferably CCCA, CCCACC, or CCCACCC; more preferably CCCACC or CCCACCC; most preferably CCCACCC. Any stretch of nucleic acid residue denoted by either R group, where n is greater than 1, may be either a heteropolymer or a homopolymer. Preferably, the R groups are each less than about five nucleotides; more preferably, less than about 10 nucleotides; yet more preferably, less than about 25 nucleotides; and most preferably, less than about 50 nucleotides. Preferably, n and m are each between 1 and 4; and more preferably, can each be up to about 10.

The present invention also includes the substantially purified polynucleotide having the sequence CCCACC, CCCA, or CCCACCC. Preferably, the sequence is CCCA; more preferably, the sequence is CCCACC; yet more preferably, the sequence is CCCACCC.

The following examples include recitation of various vectors, all of which were derived from spleen necrosis virus (SNV), a member of the avian reticuloendotheliosis virus (REV) family. Domburg, R., *Gene Ther.*, 2:301–310 (1995). Plasmid names set forth in the examples are prefixed with the letter p (e.g., pRD18) to distinguish them from virus (e.g. RD18) encoded by the same construct. The gene encoding hygromycin B phosphotransferase is referred to as hygro. Gritz et al., *Gene*, 25:189–198 (1983). The antibiotic resistance phenotype conferred by hygro is referred to as Hygro®. The neomycin (G418) resistance gene is neo and its phenotype is referred to as NEO®. Shinnick et al., *Nature*, 293: 543–548 (1981). The following examples are illustrative but are not meant to be limiting of the present invention:

EXAMPLE 1
Plasmid Constructions

All plasmids were constructed by standard cloning procedures. Sambrook, et al., *CSH*, Cold Spring Harbor, N.Y (1995). The vector pJD214HY contains all regulatory sequences required for normal retrovirus replication. It expresses the hygro gene from the left LTR promoter. Vectors of the pRD line are self-inactivating (SIN); most of the U3 region of the right LTR has been deleted. The selectable gene (hygro) and all other nonretrovirus sequences (e.g. internal promoters an internal polyadenylation signal) are in the opposite orientation as vector transcription. Plasmids pRD33 and pRD48 were derived from pRD48, which has been described previously. Domburg and Temin, *J. Virol.*, 64: 886–889 (1990); Domburg and Temin, *Mol. Cell Biol.*, 10:68–74 (1990); Domburg and Temin, *Mol. Cell Biol.*, 8:2328–233 (1988). Plasmid pRD33 was made by inserting the neo gene in the BamHI site between the vector's two internal promoters. Plasmid pRD48 contains the murine leukemia virus (MLV) encapsulation sequence (Pst1-Ball fragment, map units 0.563 to 0.747) instead. Domburg and Temin, *J. Viro.*, 64: 886–889 (1990); Domburg and Temin, *Mol. Cell Biol.*, 10:68–74 (1990); Domburg and Temin, *Mol. Cell Biol.*, 8:2328–233 (1988). Each vector's insert is in the same site as hygro.

EXAMPLE 2
Cells

D17 dog cells and D17 C3A2 dog helper cells were grown as previously described. Olson et al., *J. Virol.*, 66: 1336–1343 and Olson et al.,*J. Virol.*, 68: 7060–7066 (1994). The C3A2 helper cells were derived from D17 cells and supply all retrovirus proteins essential for virus replication without production of replication-competent helper virus. Dornburg, R., *Gene Ther.*, 2:301–310 (1995); Watanabe and Temin, *Mol. Cell Biol.*, 3:2241–2249 (1983). Selection of Hygro® cell colonies were performed in medium containing hygromycin B at 80 mg/ml.

EXAMPLE 3
Transfections and Infections

Transfections were performed by the polybrene-dimethyl sulfoxide method, as taught by Kawai and Nishizawa, *Mol. Cell. Biol.*, 4:1172–1174 (1984). Virus titers were determined on D17 cells as described previously by Olson et al., *J. Virol.*, 66: 1336–1343 and Olson et al., *J. Virol.*, 68: 7060–7066 (1994), and are expressed in terms of colony forming units per milliliter (CFU/ml) of tissue culture supernatant medium. In all experiments, virus was harvested from cells after selection for drug resistance.

EXAMPLE 4
DNA Isolation

Chromosomal DNAs were isolated by standard proteinase K digestion and phenol-chloroform extractions, as set forth in Sambrook et al., Cold Spring Harbor, N.Y. (1995).

EXAMPLE 5
Sequencing

All sequencing was performed using the Sequenase V2.0 (USB) dideoxy chain termination kit following the protocol recommended by the supplier, which is essentially the same protocol as taught by Sambrook et al., supra.

EXAMPLE 6
PCR Amplification

Amplifications were performed in 100 ml reactions using Taq DNA polymerase (Promega) or Vent DNA polymerase (New England Biolabs) in buffers supplied by the vendor. Twenty-five amplification cycles were performed on 10 micrograms of genomic DNA. Reaction cocktails included 50 picomoles of each primer, 400 mM dNTPs, 3% BSA, 2 mM $MgSO_4$ and 5 units of enzyme. Cycle parameters included a four minute pre-melt at 94° C., a final extension at 72° for five minutes, and a core cycling program (94° C., 1'; 56° C., 30"; 72° C., 2'). After amplification, fragments were resolved on a 1% agarose gel and GeneClean™ (Bio101) purified. Any additional enzyme modifications required for cloning the amplified fragment were performed prior to electrophoresis.

EXAMPLE 7
Library Construction

The pRD17.GEN-A and pRD17.GEN-B libraries contain D17 cell genomic DNA cloned into a pRD17 vector backbone. D17 DNA to be used for library construction was digested with Sau3A1 and size-selected by HPLC using a WATERS GenPack column. Fractions containing fragments smaller than 400 bp were pooled and the DNA was ligated into pRD17's unique BamHI site (FIG. 1). Transformation was performed using *E. coli* DH5 alpha cells. Cell aliquots were plated for isolation of individual clones and determination of library complexity. Approximately 500 clones were recovered from the GEN-A library and 5000 from the GEN-B library. Library complexity was gauged by miniprepping 20 random clones from each library and examining the size range of inserts by restriction mapping. More than 80% of clones examined had detectable inserts (i.e., size of inserts were greater than 50 bp) and no redundancies were observed.

EXAMPLE 8

To analyze the unusually high frequency of retroviral vector reconstitution in more detail and to identify specific sequences that trigger this process, a retroviral vector derived "recombination activator trap" (FIG. 1) was developed This trap employs the retroviral vector pRD17 which self-inactivates after one round of retroviral replication as expected. Domburg and Temin, *J. Virol.*, 64: 886–889

(1990); Dornburg and Temin, *Mol. Cell Biol.*, 10:68–74 (1990); Domburg and Temin, *Mol. Cell Biol.*, 8:2328–233 (1988). This vector contains a selectable marker gene, which confers resistance to hygromycin B (Myers and Stahl, *Annu. Rev. Genet.*, 28: 49–70 (1994)), and has been used extensively to study cDNA gene formation by retroviruses. As herein s disclosed, the DNA libraries in the vector are used as a trap for identifying recombination signals (FIG. 1, top). The insertion of a specific recombination activator (RA) is expected to trigger recombination leading to a repaired LTR Thus, subjecting such vectors to two rounds of retroviral replication enabled the identification of vector species that underwent recombination (FIG. 1), because vectors without RAs replicate only once.

A retroviral vector library was constructed by inserting size-selected (400 bases or smaller) Sau3A1-digested D17 chromosomal DNA into the BamHI site of pRD17 (FIG. 1). After transformation, the number of inserts was determined by analyzing plasmid DNAs recovered from 20 bacterial clones. The rest of the bacterial colonies which contained more than 5,000 unique inserts were pooled and plasmid DNAs were isolated. When this plasmid vector-library was subjected to the experimental protocol (FIG. 1), about 200 hygromycin resistant colonies were detected after the second round of retroviral replication. A smaller library containing about 500 random sequences failed to produce any retroviral vectors with reconstituted LTRS. Latter data indicates that the small library did not carry recombinogenic DNA sequences.

EXAMPLE 9

Figure 2A:
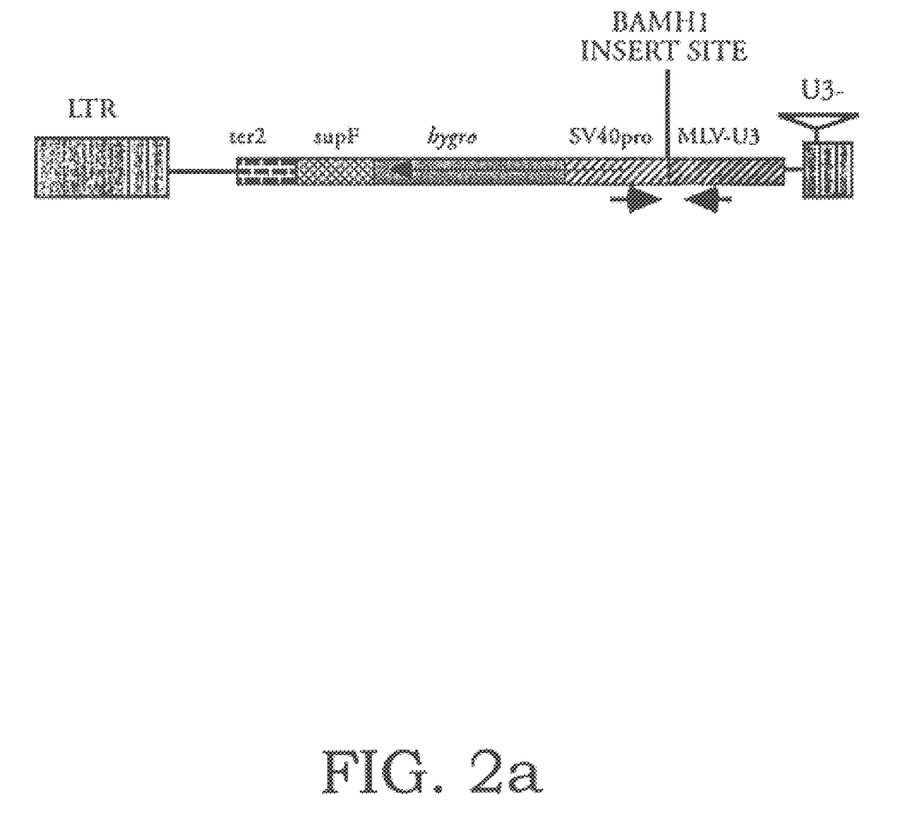
FIG. 2A is a schematic representation of the retroviral vector showing the DNA insertion site. Inserts from proviruses were sequenced.
Figure 2B:
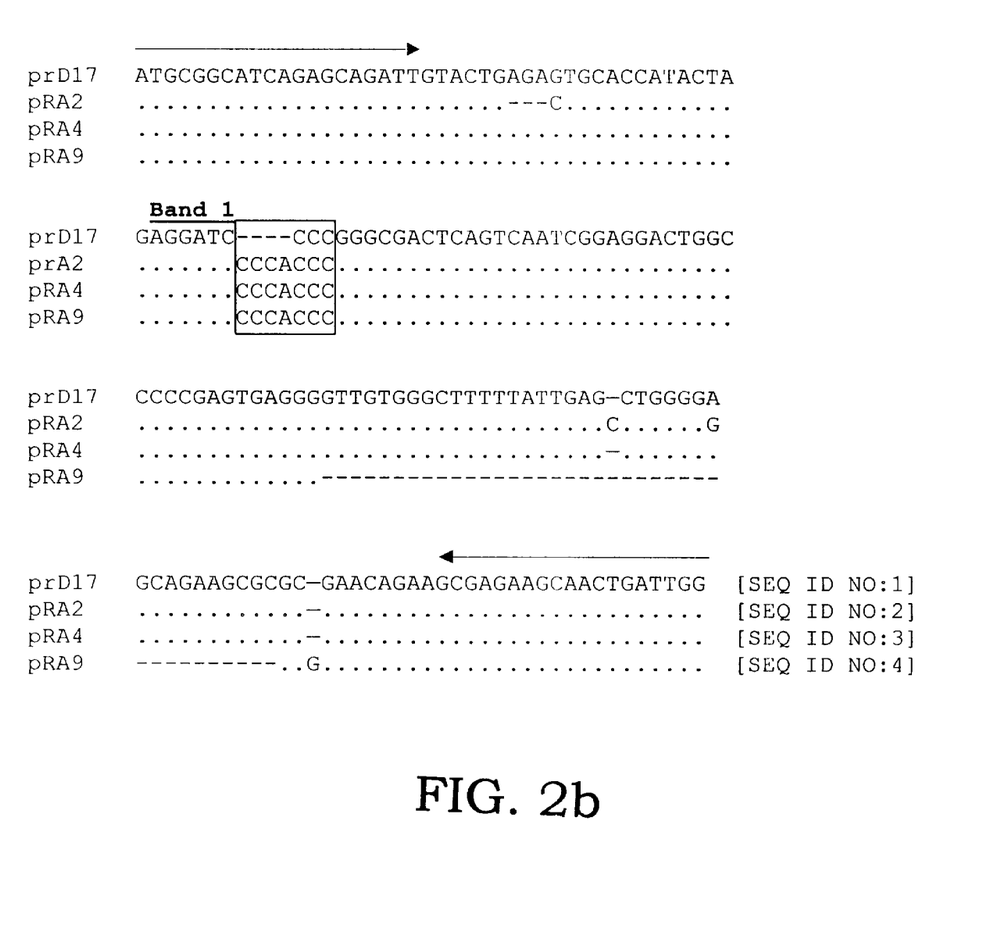
FIG. 2B shows sequences of the original vector and escaped vectors following recombination. The recombination activating sequence is boxed.

To determine whether vectors with reconstituted LTRs had an insert with a common sequence motif, the chromosomal DNAs of hygromycin resistant colonies were isolated. Inserts from vectors with reconstituted LTR were recovered by PCR amplification using primers specific for flanking vector sequences (FIG. 2). PCR products were cloned and sequenced.

Surprisingly, three vector DNAs (recovered from three separate transfections) contained only a short four nucleotide insert (CCCA) which created a symmetric sequence element, CCCACCC (FIG. 2). In each case, the clone had apparently undergone recombination which deleted the remainder of the insert because the BamHI overhang duplication necessarily created during cloning was missing. Furthermore, two out of these three clones had several mutations in the flanking DNA regions. A similar observation was also made previously when reconstituted LTRs were analyzed by DNA sequencing. Olson and Dornburg, *J. Virol.*, 68:7060–7066 (1994). Further, these data demonstrate that the amplified DNA originated from different, individual vector DNAs.

EXAMPLE 10

To test whether this seven bp motif by itself was sufficient to induce vector recombination, an oligonucleotide was cloned into pRD17. To further prove sequence specificity, a mutant form (CCCAACC) of the original heptamer was tested in parallel experiments. We noticed that the original heptamer had sequence similarity to the bacterial recombination activator chi. Furthermore, the neomycin resistance gene, which triggered LTR reconstitution with high frequency, contained both CCCACCC and chi in close proximity. Olson and Dornburg, *J. Virol.*, 68:7060–7066 (1994). Thus, the chi sequence and a mutant of chi were also tested.

Retroviral vectors containing such heptamers were again subjected to two rounds of retroviral replication as described above. We found that vectors containing the CCCACCC motif or chi elements efficiently triggered recombination leading to vectors with reconstituted LTRS. About 200 to 400 hygromycin resistant colonies were obtained after the second round of retrovimal replication (Table 1). However, no hygromycin resistant colonies were detected with vectors that contained mutant forms of the CCCACCC motif or chi. These data indicate that both the CCCACCC motif and the chi sequence can specifically enhance DNA recombination in mammalian D17 C3A2 cells.

EXAMPLE 11

Figure 3:
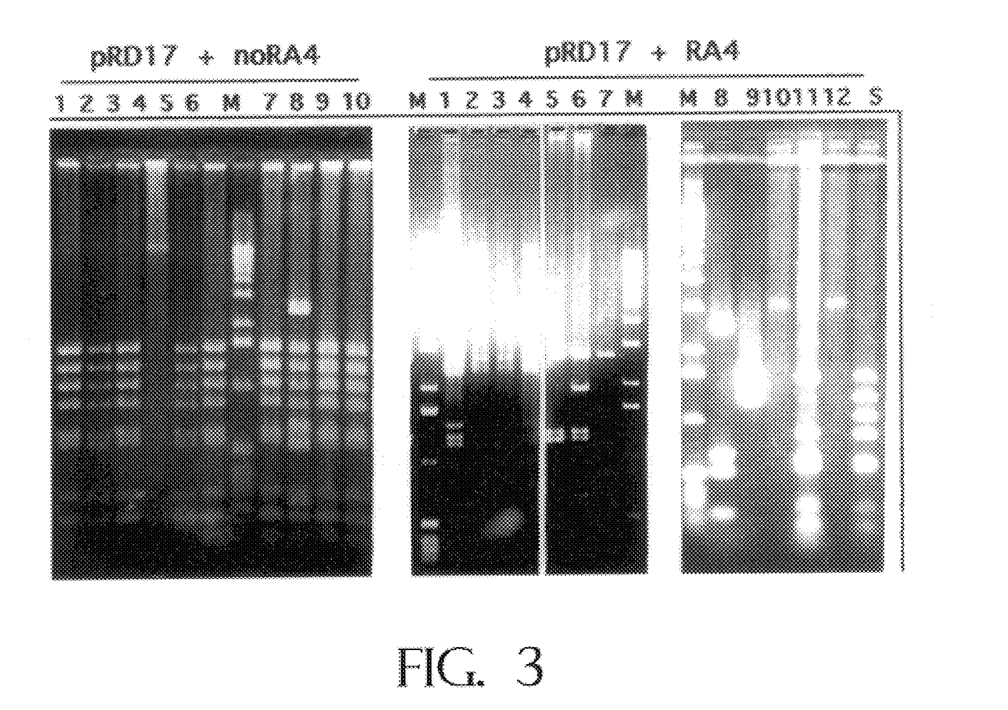
FIG. 3 is an agarose gel electrophoresis of plasmid DNA with and without the recombination activator sequence (RA4) recovered from C3A2 helper cells 42 hours after transfection and digested with restriction enzyme RsaI. M: marker DNA, S:pRD17 plasmid standard, digested with RsaI.

The CCCACCC motif activates DNA recombination within 42 hours after transfection. One concern when studying recombination in a retroviral system is whether the observed alterations are occurring on the RNA (during reverse transcription) or on the DNA level (after transfection). To exclude the possibility that LTR repair was occurring during reverse transcription, vector plasmid DNAs containing the CCCACCC motif or its mutant form were recovered forty-two hours after transfection. Hu and Temin, *Proc. Natl. Acad. Sci., U.S.A.*, 87: 1556–1560 (1990); Hu and Temin, *Science*, 250: 1227–1233 (1990). Unintegrated plasmid DNA was recovered from Step 1 C3A2 packaging cells and transformed into the recombination deficient *E. coli* host strain (SOLRÔ [Source]). Individual clones, which represent individual recombination events, were selected, plasmid DNAs were isolated, subjected to restriction analysis and compared to its parental plasmid DNA. We found that 20 out of 22 vector DNAs that contained the CCCACCC motif had undergone major rearrangements that resulted in plasmids with different restriction patterns. Rearrangements were observed only in 3 out of 22 vector clones that contained the mutant form (CCCAACC) of this motif (FIG. 3). These data show that the recombination is independent from retrovirus replication and further prove that the CCCACCC motif is a sequence-specific DNA recombination activator.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow the Sequence Listing hereof.

---

What is claimed:

1. A method for identifying a DNA sequence that promotes homologous recombination in cells comprising:
   (a) transfecting a cell culture with a self inactivating retroviral vector library containing random DNA sequence inserts, wherein the retroviral vectors include retroviral left and right long terminal repeats;
   (b) recovering from the cell culture, vectors that have undergone at least two rounds of replication; and
   (c) identifring the DNA sequence that promotes homologous recombination by identifying the random DNA sequence insert in the vector of step (b).

2. The method of claim 1 wherein the self-inactivating retroviral vector includes a mutation in the right long terminal repeat.

3. The method of claim 2, wherein the self-inactivating retroviral vector is pRD17.

4. The method of claim 1, wherein the identifying step comprises sequencing the DNA sequence insert identified in step (c).

5. The method of claim 4, wherein the cells are hosts for retroviral infection.

6. The method of claim 5 wherein the cells are metazoan cells.

7. The method of claim 6, wherein the metazoan cells are mammalian cells.

8. The method of claim 7, wherein the mammalian cells are C3A2 cells.

9. The method of claim 1, wherein the DNA sequence that promotes homologous recombination is less than 30 base pairs in length.

10. The method of claim 1, wherein the DNA sequence that promotes homologous recombination comprises a compound of the formula $$(R_1)_n\text{—}Z\text{—}(R_2)_m,$$

wherein $R_1$ and $R_2$ are respectively any nucleotide or nucleotides, n and m are the same or different and are integers between 0 and 1000, wherein at least one of n and m is non-zero, and Z is CCCA, CCCACC, or CCCACCC.

11. The method of claim 10, wherein Z is CCCACCC.

12. The method of claim 1, wherein the DNA sequence that promotes homologous recombination comprises a polynucleotide selected from the group consisting of CCCA, CCCACC, and CCCACCC.

13. A method for identifying a DNA sequence that promotes homologous recombination in cells comprising:

(a) transfecting a cell culture with a self inactivating retroviral vector library containing random DNA sequence inserts, random DNA sequence insert wherein the retroviral vectors includes retroviral left and right long ternminal repeats;

(b) recovering from the cell culture, vectors that have undergone at least two rounds of replication;

(c) identifying the DNA sequence that promotes homologous recombination by identifying the random DNA sequence insert in the vector of step (b); and (d) sequencing the identified DNA sequence insert identified in step (c), wherein the DNA sequence that promotes homologous recombination is less than 30 pairs in length.

14. The method of claim 13, wherein the DNA sequence that promotes homologous recombination comprises a compound of the formula $$(R_1)_n\text{—}Z\text{—}(R_2)_m,$$

wherein $R_1$ and $R_2$ are respectively any nucleotide or nucleotides, n and m are the same or different and are integers between 0 and 1000, wherein at least one of n and m is non-zero, and Z is CCCA, CCCACC, or CCCACCC.

15. The method of claim 14, wherein Z is CCCACCC.

16. The method of claim 13, wherein the DNA sequence that promotes homologous recombination comprises a polynucleotide selected from the group consisting of CCCA, CCCACC, and CCCACCC.

* * * * *

SEQUENCE LISTING (1) GENERAL INFORMATION:

(iii) NUMBER OF SEQUENCES: 4

(2) INFORMATION FOR SEQ ID NO:1:

```
    (i) SEQUENCE CHARACTERISTICS:
        (A) LENGTH: 160 base pairs
        (B) TYPE: nucleic acid
        (C) STRANDEDNESS: double
        (D) TOPOLOGY: linear (xi) SEQUENCE DESCRIPTION: SEQ ID NO:1:

ATGCGGCATC AGAGCAGATT GTACTGAGAG TGCACCATAC TAGAGGATCC CCGGGCGACT      60

CAGTCAATCG GAGGACTGGC CCCCGAGTGA GGGGTTGTGG GCTCTTTTAT TGAGCTGGGG     120

AGCAGAAGCG CGCGAACAGA AGCGAGAAGC AACTGATTGG                          160

(2) INFORMATION FOR SEQ ID NO:2:

(i) SEQUENCE CHARACTERISTICS:
        (A) LENGTH: 162 base pairs
        (B) TYPE: nucleic acid
        (C) STRANDEDNESS: double
        (D) TOPOLOGY: linear (xi) SEQUENCE DESCRIPTION: SEQ ID NO:2:

ATGCGGCATC AGAGCAGATT GTACTGCTGC ACCATACTAG AGGATCCCCA CCCGGGCGAC      60

TCAGTCAATC GGAGGACTGG CCCCCGAGTG AGGGGTTGTG GGCTCTTTTA TTGAGCCTGG     120

GGGGCAGAAG CGCGCGAACA GAAGCGAGAA GCAACTGATT GG                       162

(2) INFORMATION FOR SEQ ID NO:3:

(i) SEQUENCE CHARACTERISTICS:
        (A) LENGTH: 164 base pairs
        (B) TYPE: nucleic acid
        (C) STRANDEDNESS: double
        (D) TOPOLOGY: linear (xi) SEQUENCE DESCRIPTION: SEQ ID NO:3:

ATGCGGCATC AGAGCAGATT GTACTGAGAG TGCACCATAC TAGAGGATCC CCACCCGGGC      60

GACTCAGTCA ATCGGAGGAC TGGCCCCCGA GTGAGGGGTT GTGGGCTCTT TTATTGAGCT     120

GGGGAGCAGA AGCGCGCGAA CAGAAGCGAG AAGCAACTGA TTGG                     164

(2) INFORMATION FOR SEQ ID NO:4:

(i) SEQUENCE CHARACTERISTICS:
        (A) LENGTH: 127 base pairs
        (B) TYPE: nucleic acid
        (C) STRANDEDNESS: double
        (D) TOPOLOGY: linear (xi) SEQUENCE DESCRIPTION: SEQ ID NO:4:

ATGCGGCATC AGAGCAGATT GTACTGAGAG TGCACCATAC TAGAGGATCC CCACCCGGGC      60

GACTCAGTCA ATCGGAGGAC TGGCCCCCGA GTGAGGGGCG AACAGAAGC GAGAAGCAAC     120

TGATTGG                                                              127
```